(12) United States Patent
Aigner et al.

(10) Patent No.: US 7,968,742 B2
(45) Date of Patent: Jun. 28, 2011

(54) METHOD AND DEVICE FOR THE SULFONATION OR SULFATION OF SULFONATABLE OR SULFATABLE ORGANIC SUBSTANCES AND FOR PERFORMING FASTER, STRONGLY EXOTHERMIC GAS/LIQUID REACTIONS

(75) Inventors: Rudolf Aigner, Kastl (DE); Horst Reuner, Burghausen (DE)

(73) Assignee: The Chemithon Corporation, Seattle, WA (US)

( * ) Notice: Subject to any disclaimer, the term of this patent is extended or adjusted under 35 U.S.C. 154(b) by 260 days.

(21) Appl. No.: 12/158,666

(22) PCT Filed: Dec. 20, 2006

(86) PCT No.: PCT/US2006/062411
§ 371 (c)(1),
(2), (4) Date: Jun. 20, 2008

(87) PCT Pub. No.: WO2007/076401
PCT Pub. Date: Jul. 5, 2007

(65) Prior Publication Data
US 2008/0306295 A1  Dec. 11, 2008

(30) Foreign Application Priority Data
Dec. 20, 2005 (DE) .......................... 10 2005 060 816

(51) Int. Cl.
C07C 305/00 (2006.01)
B01J 35/02 (2006.01)

(52) U.S. Cl. .............................. 558/31; 558/44; 422/220

(58) Field of Classification Search .................... 558/31, 558/44; 422/220
See application file for complete search history.

(56) References Cited

U.S. PATENT DOCUMENTS

| 3,169,142 A | 2/1965 | Knaggs et al. |
| 3,427,342 A | 2/1969 | Brooks et al. |
| 3,482,947 A | 12/1969 | Jacobsen et al. |
| 3,667,919 A | 6/1972 | Denzler et al. |
| 3,839,391 A | 10/1974 | Susuki et al. |
| 3,931,273 A * | 1/1976 | Lanteri ........................... 558/33 |
| 4,072,470 A | 2/1978 | Tsuto et al. |
| 4,165,360 A | 8/1979 | Casper et al. |
| 4,183,897 A | 1/1980 | Lanteri |
| 4,261,916 A | 4/1981 | Crosby |
| 4,335,079 A | 6/1982 | Vander Mey |
| 5,117,032 A * | 5/1992 | Fabry et al. .................... 558/34 |
| 5,445,801 A * | 8/1995 | Pisoni ........................... 422/197 |
| 6,127,571 A | 10/2000 | Mulvaney, III |

FOREIGN PATENT DOCUMENTS

| CA | 1131247 | 9/1982 |
| DE | 1 443 500 | 1/1969 |
| DE | 2138038 | 3/1972 |
| DE | 26 21 455 A1 | 12/1976 |
| DE | 27 19 956 A1 | 11/1978 |
| DE | 29 23 510 A1 | 12/1979 |
| EP | 0 293 913 B1 | 9/1991 |
| GB | 2043067 A | 10/1980 |

OTHER PUBLICATIONS

Ando et al., 2000, CAS: 132:295435.*
J. Gutierrez-Gonzalez, et al.; "Improved Mathematical Model for a Falling Film Sulfonation Reactor", Ind. Eng. Chem. Res., pp. 1701-1707, vol. 27, No. 9, 1988.
W. Herman de Groot; "Sulphonation Technology in the Detergent Industry", Kluwer Academic Publishers, pp. 148-150, chapter 5.5.7 "The Chemithon Falling-Film Reactor", 1991. Netherlands.
W. Herman de Groot; "Sulphonation Technology in the Detergent Industry", Kluwer Academic Publishers, pp. 145-146, chapter 5.5.5 "The Mazzoni Sulpho Film Reactor (Multi-Tube Falling-Film Reactor)", 1991. Netherlands.

* cited by examiner

*Primary Examiner* — Rei-tsang Shiao
(74) *Attorney, Agent, or Firm* — Marshall, Gerstein & Borun LLP

(57) ABSTRACT

A method and a device for the sulfonation or the sulfation of organic liquid raw materials with an $SO_3$/air mixture and other reaction gases in order to perform rapid, highly exothermic gas-liquid reactions in conventional thin-layer falling-film reactors are disclosed. The introduction of the $SO_3$/air mixture occurs through several feed locations, which are located within (along) the reaction tube or reaction tubes or in the annular gap of annular-gap falling-film reactors. High peak temperatures, undesirable byproducts, worsening of the color and local oversulfation or oversulfonation, which leads to side reactions, are largely avoided.

26 Claims, 6 Drawing Sheets appr.10 m appr. 10 m

METHOD AND DEVICE FOR THE SULFONATION OR SULFATION OF SULFONATABLE OR SULFATABLE ORGANIC SUBSTANCES AND FOR PERFORMING FASTER, STRONGLY EXOTHERMIC GAS/LIQUID REACTIONS

BACKGROUND

1. Field of the Disclosure

The invention concerns an improved procedure for the sulfation or sulfonation of sulfatable or sulfonatable organic substances and for performing rapid, highly exothermic gas/liquid reactions in conventional thin-layer falling-film reactors, for example, tubular reactors or annular-gap reactors, characterized by the fact that the introduction of the $SO_3$/air mixture is performed according to the invention through several feed locations within (along) the reaction tube or reaction tubes or in the annular gap of annular-gap falling-film reactors.

2. Brief Description of Related Technology

The sulfation or sulfonation of organic compounds is carried out according to current methods which consist in reacting the liquid organic starting materials with the gaseous mixtures containing $SO_3$ (for example, with conversion gas, a.k.a. converter gas). The sulfonation or sulfation reactions are highly exothermic so that, together with high local sulfur trioxide concentrations in the reaction mixture, production of oversulfonated and oversulfated products and undesirable side reactions occur, which have a considerably adverse influence on product quality.

A procedure is described in DE 2 621 455 in which, in a special mixing reactor, the organic substance to be sulfonated flows together with undiluted liquid or gaseous sulfur trioxide under turbulent mixing conditions, the reaction mixture is cooled outside the reactor, and is reintroduced into the mixing reactor. The yield and color of the reaction product are unsatisfactory.

Patent Publication DE 1 443 500 describes a device for continuous sulfonation of organic substances, the device consisting of several mixers from which the reaction mixture is passed from the previous into the next reactor with intermediate cooling and whereby here, too, dilute $SO_3$ is added. This method does dose the $SO_3$ in two steps, that is, in the first step in a less than stoichiometric amount, but this reactor system is technically expensive and has not found application either.

U.S. Pat. No. 3,482,947 describes a single-tube or multi-tube film reactor in which the raw material to be sulfonated is applied uniformly through a liquid reservoir to the inside surfaces of the reaction tubes in which another tube with a smaller diameter is located, so that an annular gap is formed, whereby the liquid is applied uniformly as a film into the reaction tube. The dilute $SO_3$ gas is introduced inside this inserted tube. The raw material film to be sulfonated comes into direct contact with the spontaneously reacting diluted $SO_3$ gas. This leads to local oversulfonation, that is, a large excess of $SO_3$ is offered to the film surface or to the liquid drops that have been formed on the surface. This leads to undesirable side reactions and to a worsening of the color of the reaction product.

In U.S. Pat. No. 3,667,919 a reactor head is described for a falling-film annular-gap sulfonation reactor with which it is possible to dose the organic raw material on the inner surface of the outer reaction tube and on the outer surface of the inner reaction tube separately. In this way, supposedly a film with uniform thickness, corresponding to the inner and outer diameter is produced, in order to avoid an excessive supply of $SO_3$ to the thinner film. With this method, too, the organic material and the $SO_3$ are brought together simultaneously, as described above, which results in oversulfonation with the disadvantages of side reactions and poor color.

In U.S. Pat. No. 3,169,142 a device is described in which in a film tubular reactor the liquid to be sulfonated is applied as a film to the inner wall and the diluted $SO_3$ gas is introduced through a nozzle into the inner tube. The outer wall of the tube is cooled and serves to remove the heat generated in the extremely fast exothermic reaction. Practically, the device is limited to only one tube; a uniform distribution both of the organic raw material as well as of the dilute $SO_3$ gas is not described. Here too the organic raw material and the $SO_3$ gas are brought together simultaneously, which, because of the local excessive concentration of $SO_3$, results in the occurrence of undesirable side reactions. Also, the temperature increases greatly because of insufficient removal of heat, which again promotes side reactions and leads to a worsening of the color of the reaction product. This device has not been used in practice either.

In Patent Publication DE 2 923 510 a method is described for the sulfonation of alkylated aromatic hydrocarbons in which the organic raw material is atomized in a special reactor (in the literature known as CHEMITHON Jet Impact Reactor) to produce a large surface, and the fine droplets formed can react with the $SO_3$. The finely distributed droplets of the reaction mixture are mixed intensively with cooled, recycled sulfonic acid (reaction mixture) that has been degassed in a cyclone and thereby cooled (quenching). The method has the disadvantage that the product stream is not cooled on the way from the reactor to the cyclone separator (separation of gas/liquid) and therefore the temperature increases greatly. This leads to darker products in comparison to the falling-film reactors in which the cooling begins directly during the reaction through the outer cooling surface. Therefore, this type of reactor is used only where the product color is of lesser importance.

In U.S. Pat. No. 4,335,079, film sulfonation is described in which the film is applied to the inside surface of a rotating sphere and the $SO_3$ gas is introduced to the film through various zones. However, the thickness of the film is not uniform enough, so that uniform sulfonation does not occur. Besides, the apparatus is too complicated and therefore it has not been applied in practice.

In "Sulfonation technology in the detergent industry", Kluwer Academic Publishers (1991), Dordrecht, Netherlands, Herman de Groot, W., p. 148, the CHEMITHON falling-film reactor is described as it is used today in the detergent industry. In this method too, the organic raw material and the $SO_3$ are combined simultaneously as described above, which leads to oversulfonation, with the disadvantages of side reactions and poorer color. Also, after a relatively short time, crusting is formed in the upper reaction zone. Cleaning of the reactor is necessary, which leads to production losses.

SUMMARY

One aspect of the disclosure provides a method and device for the sulfonation or sulfation of organic liquid raw materials with an $SO_3$/air mixture, and for performing rapid, highly exothermic gas/liquid reactions in the conventional thin-layer falling-film reactors, for example, tubular reactors or annular-gap, falling-film reactors (in the form of a double cylinder), characterized by the fact that the feeding of the $SO_3$/air mixture is distributed to more than one feed location within the reaction tube or of several reaction tubes or in the annular gap of an annular-gap, falling-film reactor, for example two feed locations.

In another aspect, the method and device can be characterized by the fact that the distribution of the $SO_3$/air mixture occurs based on the ratio of the annular surface between the reaction tube and the cross-sectional surface of the inserted tube or inserted double tube in annular-gap reactors and thus based on the diameter ratio of the reaction tube and inserted tube or the reaction double tube and inserted double tube.

In still another aspect, the method and device can be characterized by the fact that the $SO_3$/air mixture is divided so that 50-90% of the $SO_3$/air mixture is introduced in the first part of the reactor and the remaining part to 100% in the second part. For example, the second part of the $SO_3$/air mixture, 4-30%, preferably 5-20% based on the total reaction length, occurs below the feed of the first part of the $SO_3$/air mixture.

Further aspects and advantages will be apparent to those of ordinary skill in the art from a review of the following detailed description, taken in conjunction with the drawings. While the method and apparatus are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

For further facilitating the understanding of the prior art and the invention, six drawing figures are appended hereto.

DETAILED DESCRIPTION

Figure 1:
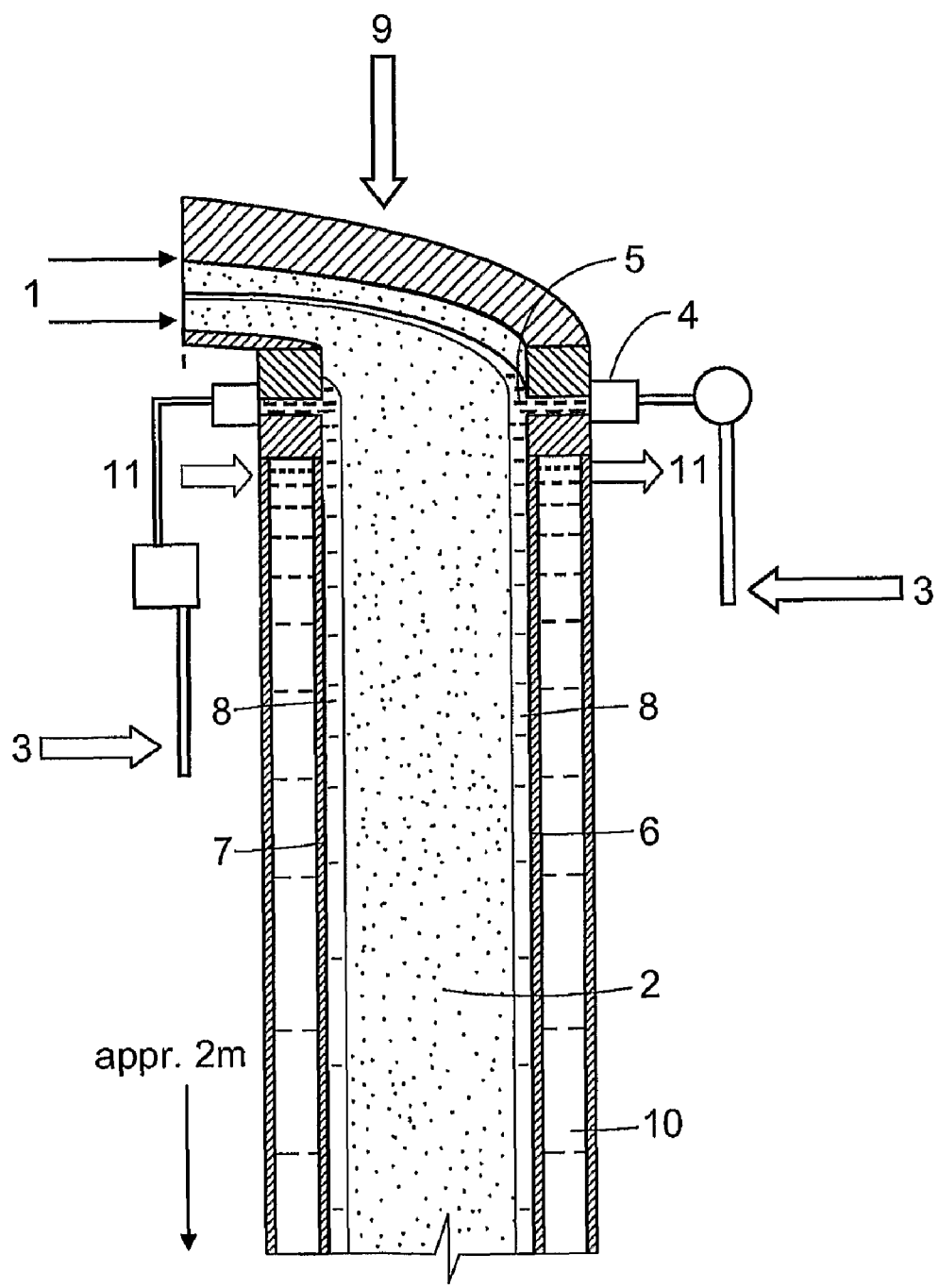
FIG. 1 shows the principle of the CHEMITHON annular-gap falling-film reactor (prior art).

The CHEMITHON annular-gap falling-film reactor (FIG. 1) consists of two short, approximately 2 meter long concentric tubes (1) which form an annular gap (2) (annular space) of approximately 5 to 10 mm. The raw material (3) is distributed uniformly via tubes and a raw material distributor (4) and through distribution slits (5) on the inner wall of the outer tube (6) and on the outer wall of the inner tube (7). The dilute, approximately 3-8 volume % $SO_3$ gas (9) is introduced into the annular gap between the raw material films (8). The large amount of heat from the reaction is removed through the cooling mantle (10) of the reaction tubes, using cooling water (11). After degassing in a cyclone and cooling in a heat exchanger, the reaction mixture is reintroduced in the lower part of the reactor for rapid cooling (quenching) of the hot reaction mixture.

In patent GB 2 043 067 a device is described for uniform feeding of the liquid mixture to be sulfated or sulfonated through a feed chamber into the reaction tubes arranged below it. It was found that uniform film formation in the tubes (BALLESTRA system) is necessary, since oversulfonation may occur if the film is thinner locally. In this document it is also described that the majority of the reaction occurs in the first part shortly after the organic raw material combines with the $SO_3$, and that a peak temperature of the reaction mass occurs there that is not acceptable. This means that in this arrangement too the organic raw material and the $SO_3$ gas are brought together simultaneously, which leads to a temperature peak shortly after the combination of the reactants and which leads to a coking directly at the feed location of the liquid raw material. Improvement is achieved only by making the raw material introduction uniform. The principle of the BALLESTRA multi-tube falling-film reactor is explained in more detail in FIG. 2.

Analogously to a tubular heat exchanger, the organic raw material (2) is applied uniformly as a raw material film (3) to the inner surface of all reaction tubes (1) (approximately 1 inch inside diameter and up to 10 m long) using a special feed system. The dilute $SO_3$ gas (4) is distributed uniformly to all the tubes from the reactor head (5). At approximately 1 m from the reactor head the reaction is completed. The cooling of the reaction mixture in the reaction chamber is carried out with cooling water (6) from the outside through two sections in the cooling mantle (7).

Figure 3:
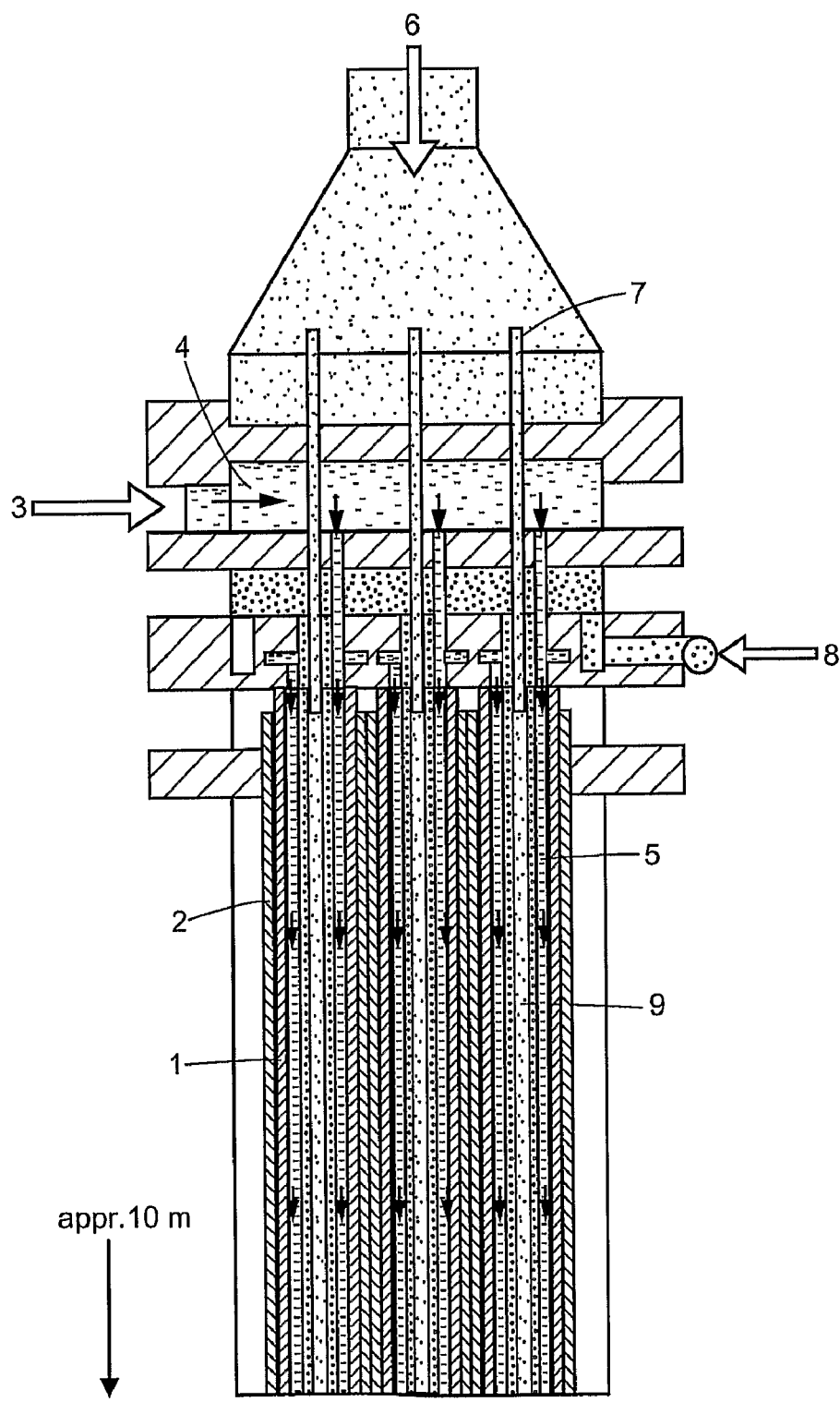
FIG. 3 shows the principle of the MAZZONI multi-tube falling-film reactor (prior art).

In U.S. Pat. No. 3,931,273 a reactor system is described, in which, in order to make the feeding of the organic raw material to be sulfonated uniform, and to reduce the reaction speed, an inert gas (equalizing gas) is dosed into each reaction tube (MAZZONI system). The diluted $SO_3$ is then combined in the desired molar ratio simultaneously with the organic raw material, for example, at a rate of 1.02 to 1.00. Here, too, local oversulfonation of the organic material occurs, because, in spite of good mixing, molecular distribution of $SO_3$ and organic raw material is not achieved. FIG. 3 describes the principle of the system of the so-called MAZZONI reactor in more detail, because this reactor type is used in industry. The MAZZONI reactor is described in U.S. Pat. No. 3,931,273 in FIG. 3.

The MAZZONI reactor is analogous to the BALLESTRA reactor with vertically-situated reaction tubes (1) which, however, in contrast to the BALLESTRA construction, each have a separate cooling mantle (2). The liquid raw material (3) is applied uniformly through a middle chamber (4) to each tube, each being applied uniformly with a ceramic-coated nozzle. To slow down the reaction in the reaction chamber (9), air (equalizing gas) (8) is brought in between the organic raw material film (5) and the diluted $SO_3$ gas (6) which is distributed into the reaction tubes through the $SO_3$ feed (7).

In DE 2 138 038 a method is described for the nearly isothermal sulfonation or sulfation of organic compounds (in the literature designated as LION T-O sulfonation falling-film reactor) in which in an annular-gap falling-film reactor (analogously to the CHEMITHON falling-film reactor) air is dosed in through a special feed device between the $SO_3$ gas stream and the thin film of the organic raw material, this serving as an air curtain which is supposed to prevent rapid diffusion of $SO_3$ into the film surface. In this way a reduction of the reaction rate is supposed to be achieved. Also, the high temperature increase in the first part of the reaction zone is supposed to be avoided in order to suppress side reactions.

As a result of the high flow velocity when the $SO_3$/air mixture meets the air curtain in the annular gap, however, a strong turbulent flow immediately occurs which immediately causes mixing of the separately-introduced sulfating gas $SO_3$/air and the "air curtain." The desired and also sensible effect of reducing the reaction rate and avoidance of the temperature peak therefore does not occur here in the desired degree to achieve a reduction of side reaction and improvement of color. The T-O film reactor is also technically complicated to execute and therefore has achieved no importance outside Japan. Also, it is used practically only for the manufacture of olefinsulfonate.

Figure 4:
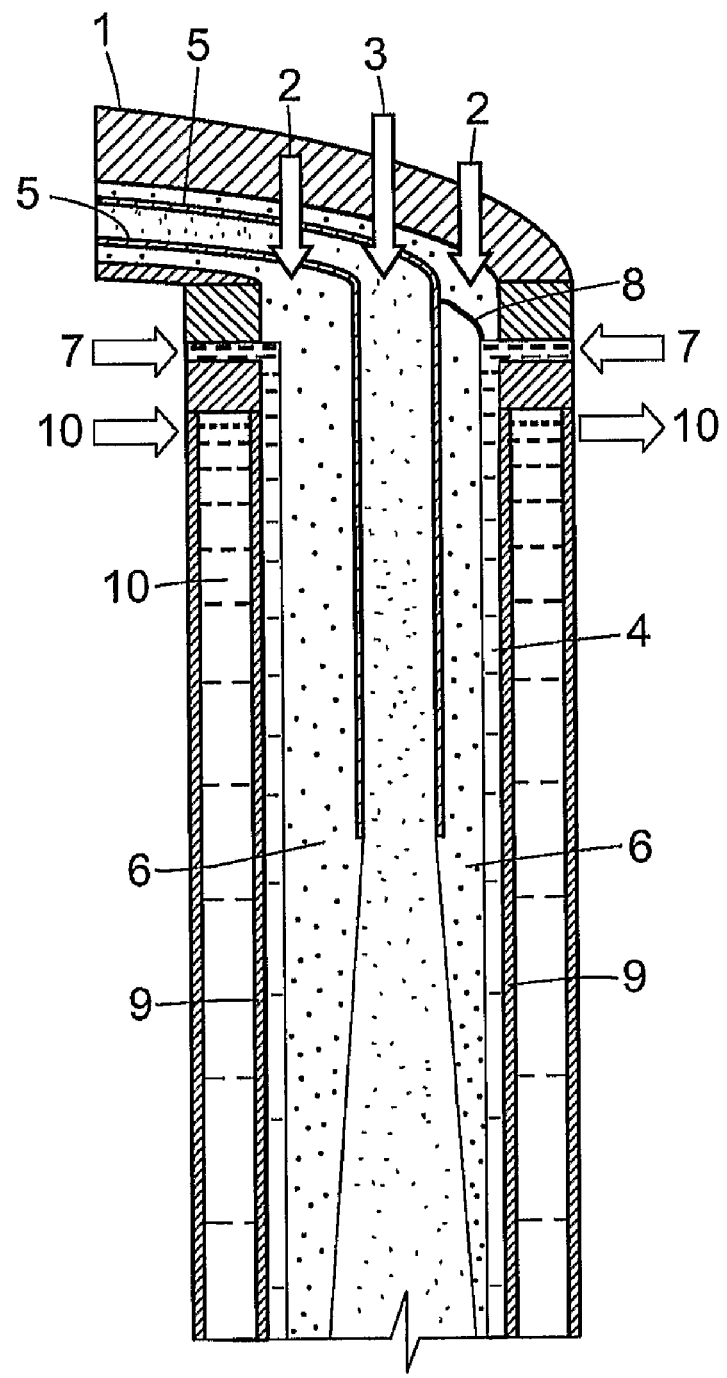
FIG. 4 shows the principle of the LION T-O annular-gap falling-film reactor (prior art).

FIG. 4 shows the principle of the LION T-O annular-gap falling-film reactor in more detail. The T-O reactor is an annular-gap falling-film reactor (similarly to the CHEMITHON reactor) with a length of approximately 2 m and a diameter of from 0.3 to 1 m corresponding to the intended capacity. Here too, the reaction mixture is quenched with an excess of recycled, cooled sulfonic acid. In contrast to the CHEMITHON reactor, using a special device at the reactor head (1), air (2) is fed between the dilute $SO_3$ gas (3) and the raw material film (4) separated by a double tube (5) open on top, in order to reduce the diffusion of $SO_3$ to the film surface and thus to slow down the reaction. Thus, the high temperature peaks should be avoided. This so-called "air curtain" (6) has the same function as the equalizing air in the MAZZONI reactor. The raw material (7) is applied to the wall of the reactor tube (9) through a distributor slit (8). The heat of reaction is removed using cooling water (10).

None of the previous methods and processes for sulfation or sulfonation of organic compounds are completely satisfactory on a large industrial scale, such as the known CHEMITHON annular-gap falling-film reactor (see FIG. 1), the BALLESTRA multi-tube falling film reactor (see FIG. 2), the MAZZONI multi-tube falling-film reactor (see FIG. 3) and the LION T-O annular-gap falling-film reactor (see FIG. 4).

Therefore the task was to provide a new apparatus and procedure for large industrial production of sulfated or sulfonated organic products, which does not have the disadvantages outlined above, such as one or more of: the occurrence of high peak temperature at the beginning of the reaction zone; crusting or coking of the reactor head; formation of undesirable by-products; worsening of the color; and local oversulfonation which leads to side reactions.

It was found, surprisingly, that this task is solved by a method characterized by the fact that the sulfonation or sulfation of organic liquid raw materials with an $SO_3$/air mixture is carried out in thin-layer falling-film reactors, for example, tubular reactors or annular-gap reactors in the form of a double cylinder, whereby the feeding of the $SO_3$/air mixture is done through several feed locations along the reaction tube or along several reaction tubes or in the annular gap of the annular-gap falling-film reactors, e.g., both at the top of the reactor and some distance further down into the reactor.

Thus, one object of the invention is a method for the sulfation or sulfonation of sulfatable or sulfonatable organic substances and for carrying out rapid highly exothermic gas/liquid reactions, which is characterized by the fact that the feeding of the $SO_3$/air mixture is carried out at several feed locations along the reaction tube or along several reaction tubes or in the annular gap of the annular-gap falling film reactors.

Figure 5:
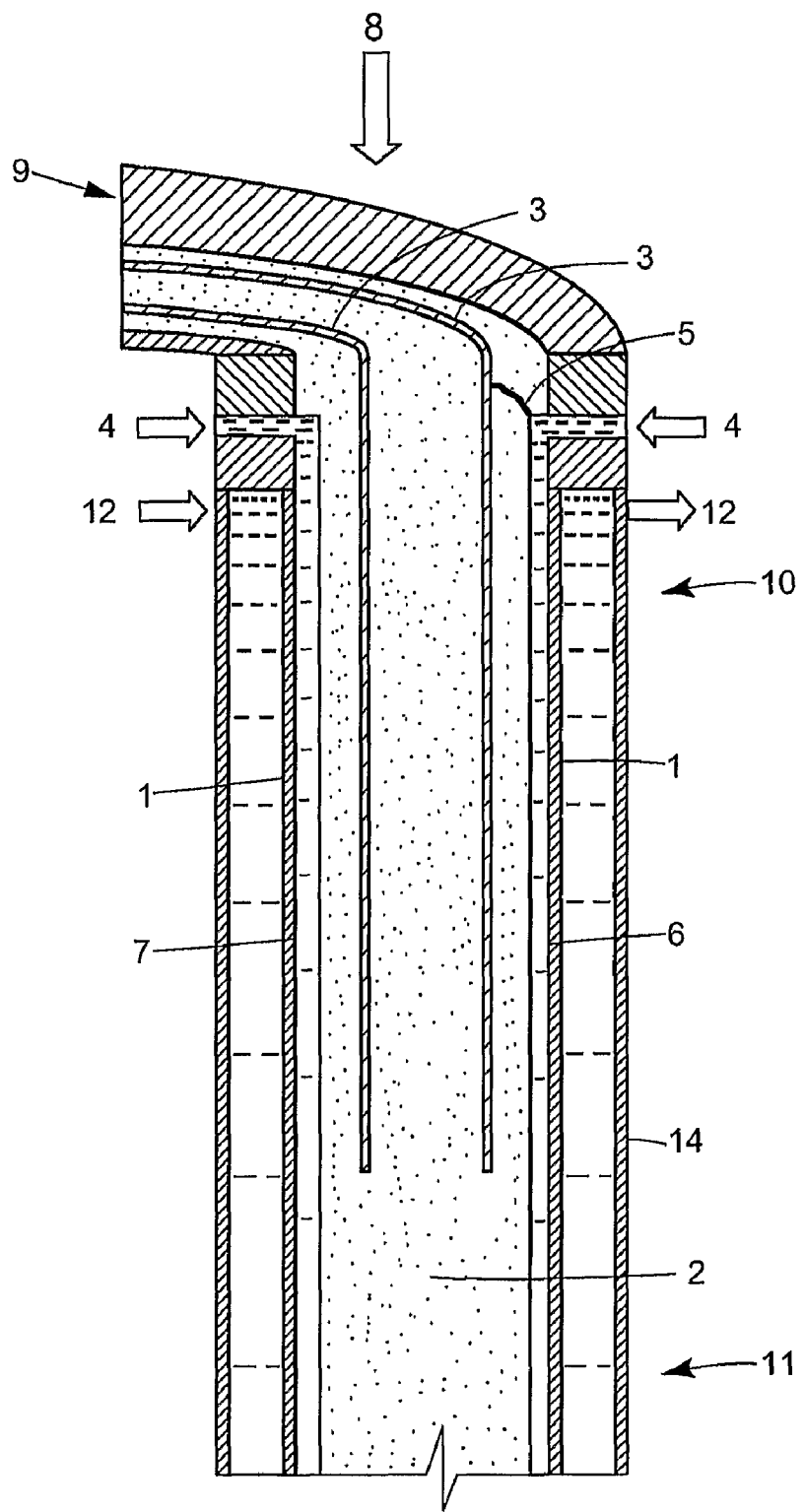
FIG. 5 is a representation of the principle of the invention for annular-gap falling-film reactors.

A preferred object of the invention is a method for the sulfation or sulfonation of sulfatable or sulfonatable organic substances and the execution of rapid, highly exothermic gas/liquid reactions in an annular-gap falling-film reactor according to FIG. 5.

In one embodiment, the design of the reactor consists of two concentric tubes (1), which form an annular gap (annular space) (2) having a thickness of about 5 mm to about 10 mm and having a length of about 1500 mm. A second set of tubes, double tube (3), with a length of only about 100 mm to about 300 mm is inserted into the top this annular gap, and preferably centered within the gap. The length of the double tube (3) is preferably about 6% to about 20% of the length of the annular gap (2) of the concentric tubes of the reactor. The ratio of the annular surface between the reaction tube and the cross-sectional surface of the inserted double tube in annular-gap reactor is preferably in a range of about 30% to about 70%.

The raw material (4) is applied uniformly through tubes and distribution slits (5) to the inner surface (6) of the outer tube and to the outer surface (7) of the inner tube. The dilute about 3% to about 8 volume % $SO_3$ gas (8) is brought into contact with the organic material through the reactor head (9) into the annular gap (2) and into the inserted double tube (3) of the reactor open on top (upper reaction zone) (10). The inserted double tube (3) distributes the $SO_3$ gas also into a lower reaction zone (11) lying further below in the reactor. In this way the reaction is divided into two stages. Thus, both the annular gap (2) at the top of the reactor and the inserted double tube (3) are both in gaseous fluid communication with a source of $SO_3$ gas (8). The entire reactor head (9) can also be in gaseous fluid communication with a source of $SO_3$ gas (8). The heat of reaction is removed with cooling water (12) in a cooling mantle (14). The high temperature peak and oversulfonation or oversulfation with the described disadvantages are avoided.

Figure 6:
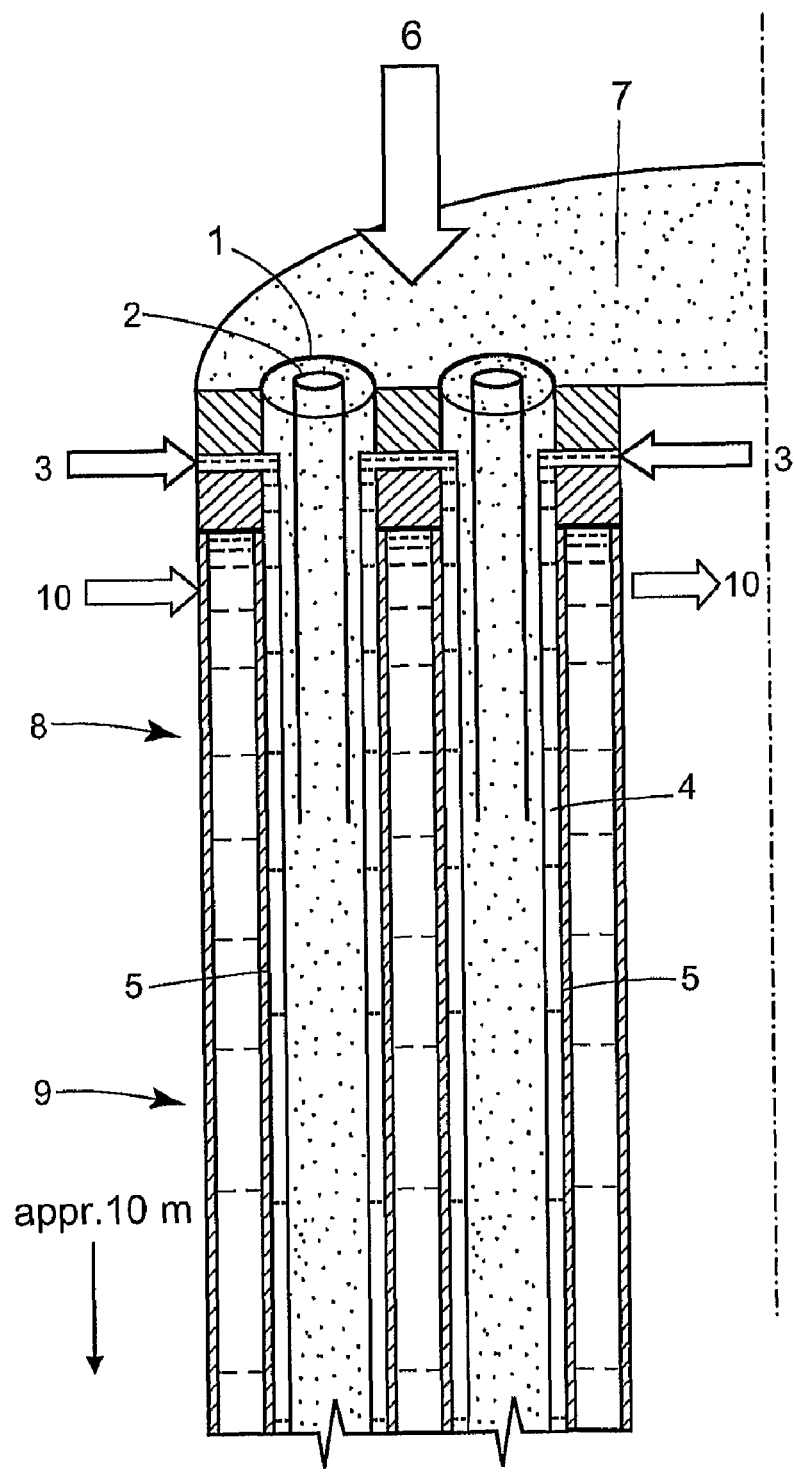
FIG. 6 is a representation of the principle of the invention for two step tube falling-film reactors.

Another preferred object of the invention is an apparatus and method for the sulfation or sulfonation of sulfatable or sulfonatable organic substances and for performing fast, highly exothermic gas/liquid reactions in a multi-tube falling-film reactor according to FIG. 6.

In a tubular system similar to a tubular heat exchanger (approximately 25 mm inside diameter, up to 10 m in length) another thin insertion tube (2) (about 100 mm to about 400 mm in length) is inserted in each reactor tube (1) at the top of each tube (1) and preferably centered within the tube (1). The length of the insertion tube (2) is preferably about 1% to about 4% of the length of the reactor tube (1). The ratio of the annular surface between the reaction tube and the cross-sectional surface of the inserted tube is preferably in a range of about 40% to about 60%. Alternatively, the diameter ratio of the reaction tube and inserted tube is preferably in a range of about 15% to about 20%. The raw material (3) is applied uniformly through a special feed system as a raw material film (4) to the inner wall (5) of each reactor tube (1). The dilute $SO_3$ gas (6) is distributed from the reactor head (7) uniformly into all tubes (1). By means of the inserted tube, the $SO_3$ gas is also applied into a reaction zone lying further down in the reactor. In this way, the reaction is divided into two stages, an upper reaction zone (8) and a lower reaction zone (9). Thus, both the inlet of each reactor tube (1) at the top of the reactor and the inserted tube (2) are both in gaseous fluid communication with a source of $SO_3$ gas (6). The entire reactor head (7) can also be in gaseous fluid communication with a source of $SO_3$ gas (6). The heat of the reaction is removed with cooling water (10). The high temperature peak and oversulfonation or oversulfation are avoided.

With the method according to the invention the reaction can be carried out in a multi-step, e.g., a two-step, manner, so to speak as a cascade, whereby in the first stage only a part of the necessary (stoichiometrically desirable) $SO_3$ gas is offered, and thus the reaction is slowed down at the beginning of the reaction. Since the reaction is carried out at the beginning with a less than stoichiometric amount of $SO_3$, local oversulfonation does not occur, the evolution of heat of reaction is considerably reduced as a result, so that the high temperature increase in the first part of the reactor is avoided. In addition, the viscosity of the reaction mixture increases more slowly (the sulfonated product has a significantly higher viscosity than the organic raw material used), which results in an improvement of the removal of the heat by the cooling water on the outer surface of the reactor. In this way, the highly exothermic reaction and the temperature of the reaction mixture can be controlled better.

This can be achieved simply for multi-tube falling-film reactors by the insertion of another tube into the inner space of the reaction tube, through which the $SO_3$/air mixture streaming from above is introduced. A part of the gas is combined directly with the raw material on top between the inserted tube and the reaction tube in which the raw material film flows on the inside. The other part of the gas is reacted with the partially sulfonated reaction product through the inner tube further down. The ratio of reaction gas between the first reaction stage and the second reaction stage can be adjusted via the diameter of the reaction tube and the diameter of the inserted tube (ratio of the annular surface between the reaction tube and the cross-sectional area of the inserted tube). The degree of conversion of the first part of the reaction and the residual conversion in the second part of the reaction can be adjusted via the length of the inserted tube.

In the case of annular-gap falling-film reactors in which the organic raw material is dosed at the inner wall of the outer tube and on the outer wall of the inner tube through a slit and runs down the walls as a film, a double tube is introduced into the annular gap in the annular-gap reactor, into which a part of the sulfonating gas is introduced into the part of the reactor lying further down and there combined with the partially sulfonated reaction mixture. In the upper part of the reactor, a part of the gas is combined directly with the organic raw material. The ratio of reaction gas between the first and second reaction stage is adjusted via the annular gap surface area of the reactor and the annular gap surface area of the inserted double tube.

Since a large part of the reaction occurs already in the first part of the reaction zone, the inserted tubes (multi-tube falling-film reactor) and the inserted double tube in the annular-gap falling-film reactor are relatively short (about 30 cm to about 40 cm) so that the incorporation is easy from a construction perspective.

With the device according to the invention a great variety of organic substances can be reacted with $SO_3$, such as, for example, alkylbenzenes with 8 to 22 carbon atoms in the alkyl chain, which can be linear or branched, saturated or unsaturated, α-olefins with 8 to 30 carbon atoms, fatty alcohols with 8 to 24 carbon atoms, alkylene oxide adducts of fatty alcohols with 8 to 24 carbon atoms, alkylphenols with 8 to 15 carbon atoms and their alkylene oxide derivatives, as well as fatty acid methyl esters.

The method and apparatus can be adapted to the reactor types used in practice mentioned above.

EXAMPLES

The following examples are provided for illustration and are not intended to limit the scope of the invention.

Comparison Example 1

Preparation of Laureth (2EO) Sulfate, Sodium Salt in an Annular-gap Falling-film Reactor According to Conventional Methods In a conventional annular-gap falling-film reactor with a diameter of 5 inches and a reactor length of approximately 2 m with an annular gap width (annular space) of 6.5 mm and with one raw material distributor slit each on the inner wall of the outer tube and on the outer wall of the inner tube and each with a cooling mantle (see FIG. 2), a C12/14 fatty alcohol ethoxylate (fatty alcohol C12 content 70-75%, C14 content 25-30%, molecular weight 194 with 2 moles of ethylene oxide (molecular weight 282, APHA color number Hazen=14) was applied uniformly onto the two annular gap surfaces through the two distributor slits in an amount of 259 kg/h (mass flow meter) (=0.920 kmol/h of fatty alcohol ethoxylate) at a temperature of 40° C. The cooling water feed temperature was adjusted to 15° C. on both cooling mantles. The diluted $SO_3$ was produced by combustion of sulfur to $SO_2$ and subsequent oxidation to $SO_3$.

Using a feed tube, 0.888 kμmol/h of dilute $SO_3$ gas ($SO_3$/raw material=0.965) was introduced into the annular gap at a concentration of approximately 3.490 volume %. After degassing in a cyclone and cooling in a heat exchanger, the reaction mixture was brought to the lower part of the reactor for rapid cooling (quenching) of the hot reaction mixture. Temperature measurements in the annular gap showed that a temperature maximum of 130° C. occurred at approximately 115 mm from the feed of the fatty alcohol ethoxylate. The exit temperature at the end of the annular gap before quenching was 40° C. The degassed sulfonic acid which was removed from the reactor continuously was neutralized with sodium hydroxide (18 weight %), demineralized water, and sodium carbonate as buffer in a special dynamic mixer so that an approximately 70% paste was obtained. The product showed the following data:

TABLE 1

| | |
|---|---|
| Active material content according to Epton (molecular weight = 384.0 g/mol): | 69.20% |
| Sodium sulfate content: | 0.10% |
| APHA color number 25% active material/$H_2O$: | 50 |
| Dioxane based on 100% active material: | 60 ppm |
| Unsulfated part as such (TLC): | 2.4 weight % (3.47% basedon100%) |
| pH value 5% active material in water: | 8.7 |

After 5 days of running, the reactor had to be opened and cleaned because the color of the product was worsening. At the reactor head, directly where the liquid raw material and $SO_3$ met, black crusting was observed which had to be washed off with dilute sodium hydroxide. The entire sulfation installation had to be shut down for 6 hours for this purpose.

Example 1

Preparation of Laureth (2EO) Sulfate, Sodium Salt in an Annular-gap Falling-film Reactor According to the Invention In the embodiment of an annular-gap falling-film reactor according to FIG. 5, a thin-walled (approx. 0.5 mm) double tube (3) having an outside diameter 124.1 mm, inside diameter 116.9 mm, and gap of 2.6 mm was built centered into the annular gap (annular space) (2). The overall tube distance (wall thickness plus gap) was 3.6 mm and the length was 330 mm. The diameter of the reactor (inside diameter of the outer tube(1)) was 5 inches (127 mm) with a reactor length of 1650 mm, with an annular gap (2) width of 6.5 mm, each having a raw material (4) distributor slit (5) on the inner wall (6) of the outer tube (1) and on the outer wall (7) of the inner tube (1) and each with a cooling mantle (14) (see FIG. 5). The diameter of the inner double tube (3) was dimensioned so that the $SO_3$ gas was introduced in an amount of 50% through the annular gap (2) in the upper reaction zone (10) and 50% through the double tube (3).

A feed (4) comprising a C12/14 fatty alcohol ethoxylate (fatty alcohol C12 content 70-75%, C14 content 25-30%, molecular weight 194) with 2 mol of ethylene oxide (molecular weight 282, APHA color number=14) were introduced through the two distributor slits (5) in an amount of 259 kg/h (mass flow meter) (=0.920 kmol/h of fatty alcohol ethoxylate) at a temperature of 40° C. uniformly onto the two annular gap surfaces (6) and (7). The cooling water (12) feed temperature on the two cooling mantles (14) was adjusted to 15° C. The dilute $SO_3$ (8) was produced by combustion of sulfur to $SO_2$ and subsequent oxidation to $SO_3$. Using a feed tube (3), 0.888 kmol/h of dilute $SO_3$ gas was introduced through the reactor head (9) into the annular gap (2) at a concentration of 3.490 volume %. After degassing in a cyclone and cooling in a heat exchanger, the hot reaction mixture was introduced into the lower part of the reactor for rapid cooling (quenching).

Temperature measurements in the annular gap showed that a first temperature maximum of 60° C. occurred at 120 mm from the feed of the fatty alcohol ethoxylate. A second temperature peak at a temperature of 55° C. occurred at approximately 450 mm. The exit temperature at the end of the annular gap before quenching was 35° C. The degassed sulfonic acid was removed continuously from the reactor and was neutralized as in the comparison experiment with sodium hydroxide (18 weight %), demineralized water, and sodium carbonate as buffer in a special dynamic mixer so that an approximately 70% paste was produced. The product has the following data:

TABLE 2

| | |
|---|---|
| Active material content according to Epton (molecular weight = 384.0 g/mol): | 69.20% |
| Sodium sulfate content: | 0.10% |
| APHA color number 25% active material/$H_2O$: | 25 |
| Dioxane based on 100% active material: | 9 ppm |
| Unsulfated part as such (TLC): | 2.4 weight % (3.47% based on 100%) |
| pH value 5% active material in water: | 8.7 |

After 4 weeks of running, the reactor was opened. No crusting was observed at the reactor head directly where the liquid raw material and $SO_3$ meet. The color of the product from the running production had not worsened either. The installation would not have had to have been shut down.

Comparison Example 2

Preparation of Laureth (3EO) Sulfate, Sodium Salt, Liquid in an Annular-gap Falling-film Reactor According to the Conventional Method In a conventional annular-gap falling-film reactor as in Comparison Example 1, with a diameter of 5 inches (127 mm) and a reactor length of approximately 1650 mm, with an annular gap width of 6.5 mm and one raw material distributor slit each on the inner wall of the outer tube and on the outer wall of the inner tube and each having a cooling mantle (see FIG. 1), a C12/14 fatty alcohol ethoxylate (fatty alcohol=ALFOL C12/C14, C12 content 51-57%, C14 content 41-47%, molecular weight 196) with 3 mol of ethylene oxide (molecular weight 328, APHA color number=30) were introduced through the two distributor slits in an amount of 297 kg/h (mass flow meter) (=0.906 kmol/h of fatty alcohol ethoxylate) at a temperature of 40° C. uniformly onto the two annular gap surfaces. The cooling water feed temperature on the two cooling mantles was adjusted to 15° C. The dilute $SO_3$ was produced by combustion of sulfur to $SO_2$ and subsequent oxidation to $SO_3$.

Using a feed tube, 0.888 kmol/h of dilute $SO_3$ gas ($SO_3$/raw material=0.980) was introduced at a concentration of 3.490 volume %. After degassing in a cyclone and cooling in a heat exchanger, the reaction mixture was reintroduced into the lower part of the reactor for rapid cooling (quenching) of the hot reaction mixture. Temperature measurements in the annular gap showed that a maximum temperature of 125° C. occurred at 120 mm from the feed of the fatty alcohol ethoxylate. The exit temperature at the end of the annular gap before quenching was 38° C. The degassed sulfonic acid, which was removed continuously from the reactor, was neutralized with sodium hydroxide (18 weight %), demineralized water, and sodium carbonate as buffer in a special dynamic mixer so that a 27% solution was obtained. The product has the following data:

TABLE 3

| | |
|---|---|
| Active material content according to Epton (molecular weight = 268): | 26.8% |
| Sodium sulfate content: | 0.1% |
| APHA color number as such: | 90 |
| Dioxane based on 100% active material: | 90 ppm |
| Unsulfated content as such: | 0.65 weight % (=2.43% based on 100%) |

After 8 days of running, the reactor had to be opened and cleaned because the color of the product was worsening. At the reactor head, directly where the liquid raw material and $SO_3$ meet, black crusting was observed which had to be washed off with dilute sodium hydroxide. The entire sulfation installation had to be shut down for 6 hours for this purpose.

Example 2

Preparation of Laureth (3EO) Sulfate, Sodium Salt, Liquid in an Annular-gap Falling-film Reactor According to the Invention In the embodiment of an annular-gap falling-film reactor, a thin-walled double tube with a tube distance (gap) of 3.6 mm and a length of 330 mm was incorporated into the annular gap. The diameter of the reactor was 5 inches (127 mm) with a reactor length of 1650 mm and an annular gap width of 6.5 mm, with one raw material distributor slit each on the inner wall of the outer tube and on the outer wall of the inner tube and each having a cooling mantle (see FIG. 5).

A C12/14 fatty alcohol ethoxylate (fatty alcohol=ALFOL C12/C14, C12 content 51-57%, C14 content 41-47%, molecular weight 196) with 3 mol of ethylene oxide (molecular weight 328, APHA color number=10) were introduced through the two distributor slits in an amount of 297 kg/h (mass flow meter) (=0.906 kmol/h of fatty alcohol ethoxylate) at a temperature of 40° C. uniformly onto the two annular gap surfaces. The diameters of the inner double tube were dimensioned so that the $SO_3$ gas was introduced in an amount of 50% through the annular gap and 50% through the double tube. The cooling water feed temperature on the two cooling mantles was adjusted to 15° C. The dilute $SO_3$ was produced by combustion of sulfur to $SO_2$ and subsequent oxidation to $SO_3$. Using a feed tube, 0.888 kmol/h of dilute $SO_3$ gas was introduced into the annular gap at a concentration of 3.490 volume %. After degassing in a cyclone and cooling in a heat exchanger, the reaction mixture was reintroduced into the lower part of the reactor for rapid cooling (quenching) of the hot reaction mixture.

Temperature measurements in the annular gap showed that a first temperature maximum of 55° C. occurred at 100 mm from the feed of the fatty alcohol ethoxylate. A second temperature peak of 50° C. occurred at approximately 250 mm. The exit temperature at the end of the annular gap before quenching was 27° C. The degassed sulfo acid, which was removed continuously from the reactor, was neutralized as in the comparison experiment with sodium hydroxide (18 weight %), demineralized water, and sodium carbonate as buffer in a special dynamic mixer so that a 27% solution was produced. The product has the following data:

TABLE 4

| | |
|---|---|
| Active material content according to Epton (molecular weight = 430 g/mol): | 27.10% |
| Sodium sulfate content: | 0.10% |
| APHA color number as such: | 45 |
| Dioxane based on 100% active material: | 13 ppm |
| Unsulfated content as such (TLC): | 0.56 weight % (2.4% based on 100%) |
| pH value 5% active material in water: | 8.7 |

After 4 weeks of running, the reactor was opened. At the reactor head, directly where the liquid raw material and $SO_3$ meet, no crusting was observed. The color of the product from the running production had not worsened either. The installation could have been operated further without any adverse influence on the quality.

Comparison Example 3

Preparation of α-olefinsulfonate, Sodium Salt in an Annular-gap Falling-film Reactor According to the Conventional Method In a conventional annular-gap falling-film reactor as in Comparison Example 1, with a diameter of 5 inches (127 mm) and a reactor length of 1650 mm, with an annular gap width of 6.5 mm and one raw material distributor slit each on the inner wall of the outer tube and on the outer wall of the inner tube and each having a cooling mantle (see FIG. 1), a C12/16 α-olefin (C12 max. 2%, C14=62-70%, C16 content 29-37% with a molecular weight of 214, APHA color number=30) was introduced through the two distributor slits in an amount of 156 kg/h (mass flow meter) (=0.772 kmol/h of α-olefin) at a temperature of 40° C. uniformly onto the two annular gap surfaces. The cooling water feed temperature on the two cooling mantles was adjusted to 30° C. The dilute $SO_3$ was produced by combustion of sulfur to $SO_2$ and subsequent oxidation to $SO_3$.

Using a feed tube, 0.888 kmol/h of dilute $SO_3$ gas was introduced into the annular gap at a concentration of 3.793 volume %. After degassing in a cyclone and cooling in a heat exchanger, the reaction mixture was reintroduced into the lower part of the reactor for rapid cooling (quenching) of the hot reaction mixture. Temperature measurements in the annular gap showed that a maximum temperature of 130° C. occurred at 100 mm from the α-olefin feed. The exit temperature at the end of the annular gap before quenching was 40° C. The degassed sulfonic acid, removed continuously from the reactor, was neutralized with a slight stoichiometric excess of sodium hydroxide (40 weight %), deionized water and before the connected high temperature hydrolysis and subsequent addition of sulfuric acid in a special mixer, in such a way that an approximately 42% solution of Na α-olefinsulfonate (solid) was obtained. The product has the following data:

TABLE 5

| | |
|---|---|
| Solid (2 hours/105° C.): | 42.8% |
| Sodium sulfate content (barium perchlorate method): | 1.6% |
| Iodine color number as such: | 5.3 |
| Disulfonate content: | 8.9 weight % |
| Unsulfonated content as such (residual oil): | 0.8 weight % |

After 4 days of running time, the reactor had to be opened and cleaned because the color of the product was worsening. At the reactor head, directly where the liquid raw material and $SO_3$ meet, very thick black crusting was observed which had to be washed off with dilute sodium hydroxide. The entire sulfonation installation had to be shut down for 6 hours for this purpose.

Example 3

Preparation of α-olefinsulfonate, Sodium Salt in an Annular-gap Falling-film Reactor According to the Invention In the embodiment of an annular-gap falling-film reactor, a thin-walled double tube with a tube wall distance (gap) of 6.5 mm and a length of 120 mm was incorporated into the annular gap. The diameter of the reactor was 5 inches (127 mm) and the length was 2 m with an annular gap width of 10 mm, and having one raw material distributor slit each on the inner wall of the outer tube and on the outer wall of the inner tube and each having a cooling mantle (see FIG. 5).

A C12/16 α-olefin (C12 max. 2%, C14=62-70%, C16 content 29-37% with a molecular weight of 214, APHA=30) was introduced through the two distributor slits in an amount of 165 kg/h (mass flow meter) (=0.772 kmol/h of α-olefin) at a temperature of 40° C. uniformly onto the two annular gap surfaces. The diameters of the inner double tube were dimensioned so that the 50% of the $SO_3$ gas was introduced through the annular gap and 50% through the double tube. The cooling water feed temperature on the two cooling mantles was adjusted to 15° C. The dilute $SO_3$ was produced by combustion of sulfur to $SO_2$ and subsequent oxidation to $SO_3$. Through a feed tube, 0.888 kmol/h of dilute $SO_3$ gas was introduced into the annular gap at a concentration of 3.793 volume %. After degassing in a cyclone and cooling in a heat exchanger, the reaction mixture was reintroduced into the lower part of the reactor for rapid cooling (quenching) of the hot reaction mixture.

Temperature measurements in the annular gap showed that a first temperature maximum of 70° C. occurred at 100 mm from the α-olefin feed. A second maximum of 55° C. occurred at approximately 200 mm. The exit temperature at the end of the annular gap before quenching was 38° C. The degassed sulfonic acid removed continuously from the reactor was neutralized with sodium hydroxide (40 weight %), demineralized water, and subsequent high temperature hydrolysis and addition of sulfuric acid in a special mixer in such a way that a 42% solution of Na α-olefinsulfonate (solid) was produced. The product has the following data:

TABLE 6

| | |
|---|---|
| Solid (2 hours/105° C.): | 42.5% |
| Sodium sulfate content (barium perchlorate method): | 1.2% |
| Iodine color number as such: | 2.7 |
| Disulfonate content: | 6.9 weight % |
| Unsulfonated content as such (residual oil): | 0.8 weight % (1.9% based on 100%) |

After 2 weeks of running, the reactor was opened. At the reactor head, directly where the liquid raw material and $SO_3$ meet, no crusting was observed. The color of the product from the running production was not worsened either. The installation could have been operated further without any adverse influence on the quality.

Comparison Example 4

Preparation of Laureth (2EO) Sulfate, Sodium Salt in a Single-Tube Falling-Film Reactor According to the Conventional Method In a single-tube falling-film reactor (analogous to BALL-ESTRA) the organic material was applied uniformly as a film (see FIG. 4) through a special raw material feed system to the inner surface of the tube (1 inch=25.4 mm inside diameter, 8 m long, mantle cooling with two sections) (see FIG. 4). For the experiment a C12/14 fatty alcohol ethoxylate (C12 content 70-75%, C14 content 25-30%, molecular weight 238) with 2 mol of ethylene oxide (molecular weight 282, APHA number=10) was uniformly applied through a distributor slit in an amount of 21 kg/h (mass flow meter) (=0.077 kmol/h of fatty alcohol ethoxylate) at a temperature of 40° C., to the inner wall of the reaction tube. The cooling water feed temperature on the cooling mantle was adjusted to 15° C. The dilute $SO_3$ was produced by combustion of sulfur to $SO_2$ and subsequent oxidation to $SO_3$. Using a feed tube, 0.074 kmol/h of dilute $SO_3$ gas was introduced into the reaction chamber at a concentration of 3.420 volume %. At the end of the reactor at a length of approximately 10 m the sulfo acid is degassed through a cyclone.

Temperature measurements in the reaction tube showed that a maximum temperature of 120° C. occurred at 400 mm from the fatty acid ethoxylate feed. The exit temperature at the end of the reaction tube was 40° C. The degassed sulfo acid removed continuously from the reactor was neutralized with sodium hydroxide (18 weight %), deionized water and sodium carbonate as buffer in a special dynamic mixer in such a way that a 70% paste was produced. The product has the following data:

TABLE 7

| | |
|---|---|
| Active material content according to Epton (molecular weight = 384.0 g/mol): | 70.20% |
| Sodium sulfate content: | 0.10% |
| APHA color number 25% active material/H$_2$O: | 92 |
| Dioxane based on 100% active material: | 82 ppm |
| Unsulfated part as such (TLC): | 2.2 weight % (=3.1% based on 100%) |
| pH value 5% active material in water: | 8.6 |

After 5 days of running, the reactor had to be opened and cleaned because the color of the product was worsening. At the reactor feed, directly where the liquid raw material and $SO_3$ meet, black crusting was observed which had to be washed off with dilute sodium hydroxide.

Example 4

Preparation of Laureth (2EO) Sulfate, Sodium Salt in a Single-tube Falling-film Reactor According to the Invention In a single-tube falling-film reactor (analogous to BALL-ESTRA), the organic raw material was applied uniformly, as a film through a special raw material feed system to the inner surface of the tube (1 inch=25.4 mm inside diameter, 8 m long, mantle cooling with two sections) (see FIG. 6). For the experiment a C12/14 fatty alcohol ethoxylate (C12 content 70-75%, C14 content 25-30%, molecular weight 238) with 2 mol of ethylene oxide (molecular weight 282, APHA number=10) was applied uniformly to the tube surface through a distributor slit in an amount of 21 kg/h (mass flow meter) (=0.077 kmol/h of fatty alcohol ethoxylate) at a temperature of 40° C. The cooling water feed temperature on the cooling mantle was adjusted to 15° C. The dilute $SO_3$ was produced by combustion of sulfur to $SO_2$ and subsequent oxidation to $SO_3$. Using a feed tube, 0.98 kmol/h of dilute $SO_3$ gas was introduced into the tubular reaction chamber at a concentration of 3.420 volume %, into which was incorporated an inserted tube of 0.75 inch (19.05 mm) inside diameter, a wall thickness of 0.5 mm and length of 300 mm. At the end of the reactor, the sulfo acid was degassed through a cyclone over a distance of approximately 10 m.

Temperature measurements in the reaction chamber showed that a temperature maximum of 120° C. occurred at 400 mm from the fatty alcohol ethoxylate feed. The exit temperature at the end of the reaction tube was 35° C. The degassed sulfo acid removed continuously from the reactor was neutralized with sodium hydroxide (18 weight %), demineralized water, and sodium carbonate as buffer in a special dynamic mixer in such a way that a 70% paste was produced. The product has the following data:

TABLE 8

| | |
|---|---|
| Active material content according to Epton (molecular weight = 384.0 g/mol): | 69.20% |
| Sodium sulfate content: | 0.10% |
| APHA color number 25% active material/H$_2$O: | 47 |
| Dioxane based on 100% active material: | 9 ppm |
| Unsulfated part as such (TLC): | 2.4 weight % (=3.5% based on 100%) |
| pH value 5% active material in water: | 8.7 |

After 4 weeks of running, the reactor was opened. No crusting was observed at the reactor head directly where the liquid raw material and $SO_3$ meet. The color of the product during running production was not worsening either. The installation could have been operated further without any adverse influence on the quality.

Comparison Example 5

Preparation of Laureth (3EO) Sulfate, Sodium Salt in a Single-tube Falling-film Reactor According to the Conventional Method In a single-tube-falling-film reactor (analogous to BALL-ESTRA) the organic raw material was applied uniformly through a special raw material feed system to the inner surface of the tube (1 inch=25.4 mm inside diameter, 10 m long, mantle cooling with two sections) (see FIG. 4). For the experiment a C12/14 fatty acid ethoxylate (C12 content 70-75%, C14 content 25-30%, molecular weight 196) with 3 mol of ethylene oxide (molecular weight 328, APHA number=10) was applied uniformly to the tube surface through the two distributor slits in an amount of 24 kg/h (mass flow meter) (=0.076 kmol/h of fatty alcohol ethoxylate) at a temperature of 40° C. The cooling water feed temperature was adjusted to 15° C. The dilute $SO_3$ was produced by combustion of sulfur to $SO_2$ and subsequent oxidation to $SO_3$.

Using a feed tube, 0.074 kmol/h of dilute $SO_3$ gas at a concentration of 3.420 volume % was introduced into the reaction chamber. At the end of the reactor, the sulfo acid is degassed through a cyclone over a length of approximately 10 m. Temperature measurements in the reaction tube showed that a temperature maximum occurred after 400 mm from the fatty alcohol ethoxylate feed, and it was 120° C. The exit temperature at the end of the reaction tube was 35° C. The degassed sulfo acid which was removed continuously from the reactor was neutralized with sodium hydroxide (18 weight %), demineralized water, and sodium carbonate as buffer in a special dynamic mixer in such a way that a 27% solution was produced. The product has the following data:

TABLE 9

| | |
|---|---|
| Active material content according to Epton (molecular weight = 268): | 26.8% |
| Sodium sulfate content: | 0.1% |
| APHA color number as such: | 88 |
| Dioxane based on 100% active material: | 86 ppm |
| Unsulfated part as such: | 0.65 weight % (=2.4% based on 100%) |

After 5 days of running, the reactor had to be opened and cleaned because the color of the product had worsened. At the reactor feed, directly where the liquid raw material and $SO_3$ meet, black crusting was observed which had to be washed off with dilute sodium hydroxide.

Example 5

Preparation of Laureth (3EO) Sulfate, Sodium Salt in a Single-tube Falling-film Reactor According to the Invention In a single-tube falling-film reactor (analogous to BALL-ESTRA) the organic raw material was applied uniformly as a film through a special raw material feed system to the inner surface of the tube (1 inch=25.4 mm inside diameter, 10 m long, mantle cooling with 2 sections) (see FIG. 6). For the experiment, a C12/14 fatty alcohol ethoxylate (C12 content 70-75%, C14 content 25-30%, molecular weight 196) with 3 mol of ethylene oxide (molecular weight 328, APHA number=10) was applied uniformly through the two distributor slits to the tube surface in an amount of 24 kg/h (mass flow meter)(=0.076 kmol/h of fatty alcohol ethoxylate) at a temperature of 40° C. The cooling water feed temperature was adjusted to 15° C. The dilute $SO_3$ was produced by combustion of sulfur to $SO_2$ and subsequent oxidation to $SO_3$. Through an inlet tube, 0.074 kmol/h of dilute $SO_3$ gas with a concentration of 3.420 volume % was introduced into the tubular reaction chamber into which an inserted tube with 0.75 inch=19.05 inside diameter, a wall thickness of 0.5 mm and a length of 300 mm was incorporated. At the end of the reactor over a length of about 10 m the sulfo acid was degassed through a cyclone.

Temperature measurements in the reaction tube showed that a temperature maximum of 120° C. occurred at 400 mm from the fatty alcohol ethoxylate feed. The exit temperature at the end of the reaction tube was 35° C. The degassed sulfo acid which was removed continuously from the reactor was neutralized with sodium hydroxide (18 weight %), deionized water and sodium carbonate as buffer in a special dynamic mixer in such a way that a 70% paste was produced from it. The product has the following data:

TABLE 10

| | |
|---|---|
| Active material content according to Epton (molecular weight = 430 g/mol): | 27.10% |
| Sodium sulfate content: | 0.10% |

TABLE 10-continued

| | |
|---|---|
| APHA color number as such: | 88 |
| Dioxane based on 100% active material: | 14 ppm |
| Unsulfated part as such (TLC): | 0.65 weight % (=2.4% based on 100%) |
| pH value 5% active material in water: | 8.7 |

After 4 weeks of running time, the reactor was opened. At the reactor head, directly where the liquid raw material and $SO_3$ meet, no crusting was observed. The color of the product from the running production had not worsened, either. The installation could have been operated further without any adverse influence on quality.

Comparison Example 6

Figure 2:
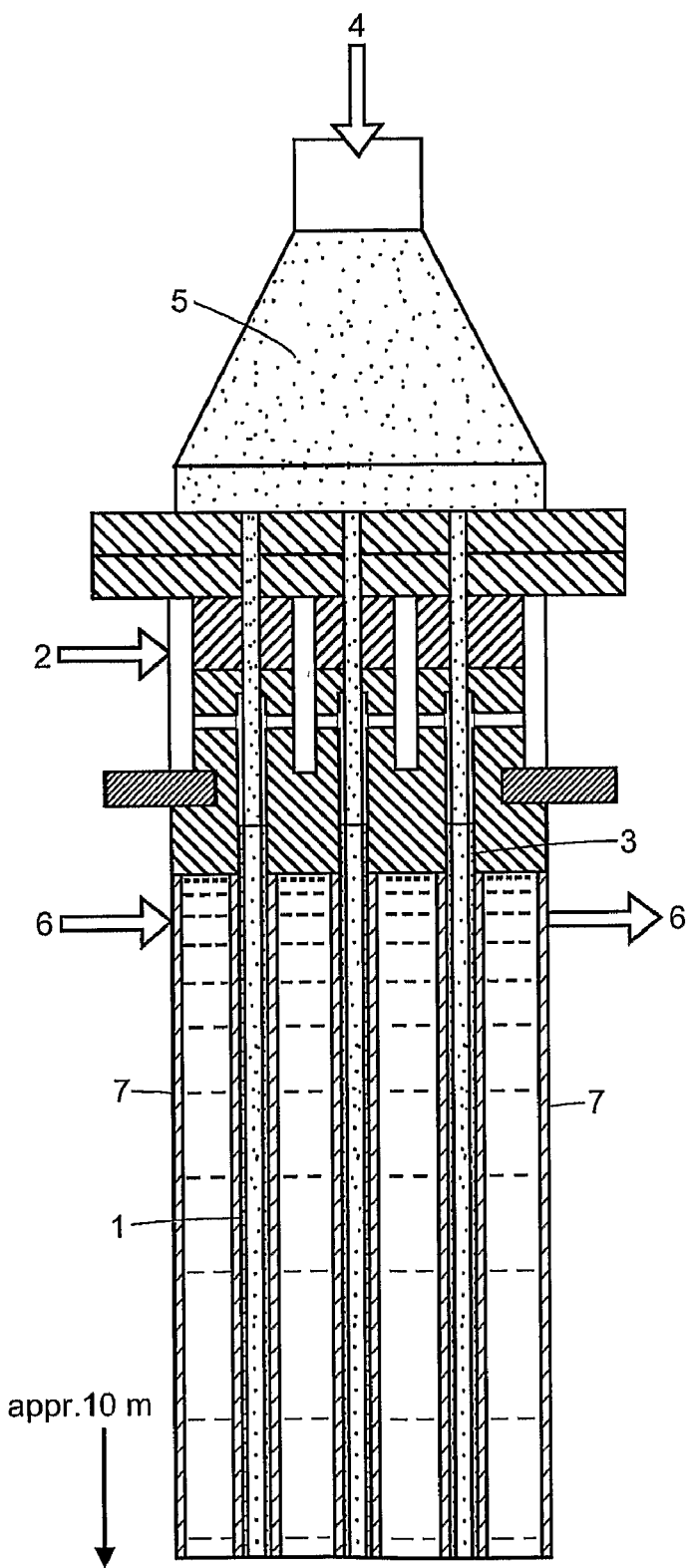
FIG. 2 shows the principle of the BALLESTRA multi-tube falling-film reactor (prior art).

Preparation of α-olefinsulfonate, Sodium Salt in a Single-tube Falling-tube Reactor According to the Conventional Method In a single-tube falling-film reactor (analogous to BALL-ESTRA) the organic raw material was applied uniformly as a film through a special raw material feed system to the inner surface of the tube (1 inch=25.4 mm inside diameter, 10 m long, mantle cooling with two sections) (see FIG. 2). For the experiment a C12/14/16 α-olefin (C12 max. 2%, C14=62-70%, C16 content 29-37%, molecular weight=214) was applied uniformly to the inner surface of the reaction tube through the distributor slit in an amount of 13 kg/h (mass flow meter) (=0.064 kmol/h) of α-olefin at a temperature of 40° C. The cooling water feed temperature was adjusted to 15° C. The dilute $SO_3$ was produced by combustion of sulfur to $SO_2$ and subsequent oxidation to $SO_3$.

Using a feed tube, 0.074 kmol/h of dilute $SO_3$ gas at a concentration of 3.664 volume % was introduced into the reaction chamber. At the end of the reactor, over a length of 10 m, the sulfonic acid was degassed through a cyclone. Temperature measurements in the reaction tube showed that a temperature maximum of 120° C. occurred at 400 mm from the α-olefin feed. The exit temperature at the end of the reaction tube was 38° C. The degassed sulfonic acid which was removed continuously from the reactor was neutralized with a slight stoichiometric excess of sodium hydroxide (40 weight %), demineralized water, and preconnected high temperature hydrolysis and subsequent addition of sulfuric acid in a special dynamic mixer in such a way that a 42% solution of Na α-olefinsulfonate (solid) was obtained. The product has the following data:

TABLE 11

| | |
|---|---|
| Solid (2 hours/105° C.): | 42.8% |
| Sodium sulfate content (barium perchlorate method): | 1.6% |
| Iodine color number as such: | 5.3 |
| Disulfonate content: | 9.0 weight % |
| Unsulfonated part as such (residual oil): | 0.8 weight % (1.9% based on 100%) |

After 5 days of running the reactor had to be opened and cleaned because the color of the product became worse. Very thick black crusting was observed at the reactor feed directly where the liquid raw material and $SO_3$ meet, and this had to be washed off with dilute sodium hydroxide.

Example 6

Preparation of α-olefinsulfonate, Sodium Salt in a Single-tube Falling-film Reactor According to the Invention In a single-tube falling-film reactor (analogous to BALL-ESTRA) the organic raw material was applied uniformly, as a film using a special raw material feed system, to the inner surface of the tube (1 inch=25.4 inside diameter, 10 m long, mantle cooling with two sections) (see FIG. 6). For the experiment a C12-16 α-olefin (C12 max. 2%, C14=62-70%, C16 content 29-37%, with a molecular weight of 214) was applied uniformly through the two distributor slits in an amount of 13 kg/h (=0.064 kmol/h of α-olefin) at a temperature of 40° C. The diameters of the inserted tube were dimensioned so that the $SO_3$ gas was introduced 50% through the reaction tube and 50% through the inserted tube. The cooling water feed temperature was adjusted to 15° C. The dilute $SO_3$ was produced by the combustion of sulfur to $SO_2$ and subsequent oxidation to $SO_3$. Through a feed tube 0.074 kmol/h dilute $SO_3$ gas at a concentration of 3.664 volume % was introduced into the tubular reaction chamber into which an inserted tube of 0.75 inch=19.05 mm inside diameter, a wall thickness of 0.5 mm and a length of 300 mm had been incorporated. At the end of a reactor over a length of about 10 m the sulfonic acid was degassed through a cyclone.

Temperature measurements in the reaction tube showed that a temperature maximum of 120° C. occurred at 400 mm from the α-olefin feed. The exit temperature at the end of the reaction tube was 45° C. The degassed sulfonic acid which was removed continuously from the reactor was neutralized with a slight stoichiometric excess of sodium hydroxide (40 weight %), demineralized water, and preconnected high temperature hydrolysis and subsequent addition of sulfuric acid in a special dynamic mixer in such a way that a 42% solution of Na α-olefinsulfonate solid was produced. The product has the following data:

TABLE 12

| | |
|---|---|
| Solid (2 hours/105° C.): | 42.5% |
| Sodium sulfate content (barium perchlorate method): | 1.2% |
| Iodine color number as such: | 2.7 |
| Disulfonate content: | 7.0 weight % |
| Unsulfonated part as such (residual oil): | 0.8 weight % (=1.9% based on 100%) |

After 4 weeks of running the reactor was opened. At the reactor head directly where the liquid raw material and $SO_3$ meet no crusting could be observed. The color of the product from running production had not worsened either. The installation could have been operated further without any adverse influence on quality.

The examples show that according to the method of the invention the color of the finished product is reduced to about half, the dioxane content in the case of ether sulfate is reduced to approximately one fourth, and that the crusting at the reactor head is avoided.

Example 7

Preparation of C12/14 alkyl diglycol ether sulfate, Sodium Salt in an Annular-gap Falling-film Reactor According to the Invention In the embodiment of an annular-gap falling-film reactor, a thin-walled double tube with a tube wall distance (gap) of 3.6 mm and 330 mm length was incorporated into the annular gap. The diameter of the reactor was 5 inches (127 mm) with a reactor length of 1650 mm and an annular gap width of 6.5 mm and there was one raw material distributor slit each on the inner wall of the outer tube and on the outer wall of the inner tube and a cooling mantle on each (see FIG. 5). The diameter of the inner double tube was dimensioned so that $SO_3$ gas was introduced 50% through the annular gap and 50% through the double tube.

A fatty alcohol ethoxylate (fatty alcohol C12 content 70-75%, C14 content 25-30%, molecular weight 194) with 2 mol of ethylene oxide (molecular weight 282, APHA color number=14) was applied uniformly to both annular gap surfaces through the two distributor slits in an amount of 252 kg/h (mass flow meter) (=0.897 kmol/h of fatty alcohol ethoxylate) at a temperature of 40° C. The cooling water feed temperature was adjusted to 15° C. on both cooling mantles. The dilute $SO_3$ was prepared by combustion of sulfur to $SO_2$ and subsequent oxidation to $SO_3$. Through a feed tube, 0.888 kmol/h dilute $SO_3$ gas ($SO_3$/raw material=0.990) at a concentration of 3.490 volume % was introduced into the annular gap. After degassing in a cyclone and cooling in a heat exchanger the reaction mixture was reintroduced into the lower reactor part for rapid cooling (quenching) of the hot reaction mixture.

Temperature measurements in the annular gap showed that a first temperature maximum of 65° C. was reached at 120 mm from the feed of the fatty alcohol ethoxylate. A second temperature peak of 55° C. occurred at about 450 mm. The exit temperature at the end of the annular gap before quenching was 35° C. The degassed sulfo acid which was removed continuously from the reactor was neutralized as in the comparison experiment with sodium hydroxide (18 weight %), demineralized water, and sodium carbonate as buffer in a special dynamic mixer in such a way that an approximately 70% paste was obtained. The product has the following data:

TABLE 13

| | |
|---|---|
| Active material content according to Epton (molecular weight = 384.0 g/mol): | 69.10% |
| Sodium sulfate content: | 0.10% |
| APHA color number 25% active material/$H_2O$: | 28 |
| Dioxane based on 100% active material: | 12 ppm |
| Unsulfated part as such (TLC): | 0.8 weight % (1.16% based on 100%) |
| pH value 5% active material in water: | 8.6 |

After 4 weeks of running the reactor was opened. No crusting was observed at the reactor head directly where the liquid raw material and $SO_3$ meet. The color of the product from the current production had not worsened either. The installation would not have had to have been shut down.

Example 8

Preparation of Laureth (3EO) Sulfate, Sodium Salt in an Annular-gap Falling-film Reactor According to the Invention In the embodiment of an annular-gap falling-film reactor, a thin-walled double tube with a tube wall distance (gap) of 3.6 mm and a length of 330 mm was incorporated into the annular gap. The diameter of the reactor was 5 inches (127 mm) with a reactor length of 1650 mm with an annular gap width of 6.5 mm and one raw material distributor slit each on the inner wall of the outer tube and on the outer wall of the inner tube and a cooling mantle on each (see FIG. 5).

A fatty alcohol ethoxylate (fatty alcohol=ALFOL C12/14, C12 content 51-57%, C14 content 41-47%, molecular weight 196) with 3 mol of ethylene oxide (molecular weight 328, APHA=10) was applied uniformly to both annular gap surfaces through the two distributor slits in an amount of 292 kg/h (mass flow meter)=0.893 kmol/h of fatty alcohol ethoxylate at a temperature of 40° C. The diameters of the inner double tube were dimensioned so that the $SO_3$ gas was introduced in an amount of 50% through the annular gap and 50% through the double tube. The cooling water feed temperature onto the two cooling mantles was adjusted to 15° C. The dilute $SO_3$ was prepared by combustion of sulfur to $SO_2$ and subsequent oxidation to $SO_3$. Through a feed tube 0.893 kmol/h ($SO_3$/raw material=0.995) of dilute $SO_3$ gas at a concentration of 3.490 volume % was introduced into the annular gap. After degassing in a cyclone and cooling in a heat exchanger, the reaction mixture was reintroduced to the lower reactor part for rapid cooling (quenching) of the hot reaction mixture.

Temperature measurements in the annular gap showed that a first temperature maximum of 65° C. occurred at 120 mm from the fatty alcohol ethoxylate feed. A second temperature peak of 55° C. occurred at about 450 mm. The exit temperature at the end of the annular gap before quenching was 35° C. The degassed sulfo acid which was removed continuously from the reactor was neutralized as in the comparison experiment with sodium hydroxide (18 weight %), demineralized water, and sodium carbonate as buffer in a special dynamic mixer in such a way that a 27% solution was obtained. The product has the following data:

TABLE 14

| | |
|---|---|
| Active material content according to Epton (molecular weight = 430 g/mol): | 27.00% |
| Sodium sulfate content: | 0.10% |
| APHA color number as such: | 48 |
| Dioxane based on 100% active material: | 14 ppm |
| Unsulfated part as such (TLC): | 0.3 weight % (1.11% based on 100%) |
| pH value 5% active material in water: | 8.6 |

After 4 weeks of running the reactor was opened. At the reactor head directly where the liquid raw material and $SO_3$ meet no crusting was observed. The color of the product during running production had not worsened either. The installation could have been operated further without any adverse influence on quality.

The foregoing description is given for clearness of understanding only, and no unnecessary limitations should be understood therefrom, as modifications within the scope of the invention may be apparent to those having ordinary skill in the art.

Throughout the specification, where compositions are described as including components or materials, it is contemplated that the compositions can also consist essentially of, or consist of, any combination of the recited components or materials, unless described otherwise.

The practice of a method disclosed herein, and individual steps thereof, can be performed manually and/or with the aid of electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, it will be apparent that some of the individual steps may be combined, omitted, or further subdivided into additional steps.

What is claimed is:

1. In a method for the sulfonation or sulfation of organic liquid raw materials with an $SO_3$/air mixture in a thin-layer, falling-film reactor comprising a tubular reactor or an annular-gap, falling-film reactor in the form of a double cylinder, the improvement comprising, introducing a first fraction of the $SO_3$/air mixture to a first feed location within a reaction tube or within the annular gap of an annular-gap, falling-film reactor and in a flow direction substantially parallel to the flow of organic liquid raw material through the falling-film reactor; and introducing a second fraction of the $SO_3$/air mixture to a second feed location within a reaction tube or within the annular gap of an annular-gap, falling-film reactor and in a flow direction substantially parallel to the flow of organic liquid raw material through the falling-film reactor, said second location distinct from the first location and spaced from the first location downstream in the direction of the falling film of organic liquid raw material, wherein the organic liquid raw material is selected from the group consisting of alkylated aromatic hydrocarbons; alkylbenzenes with 8 to 22 carbon atoms in the alkyl chain, said alkylbenzenes being linear or branched, said alkylbenzenes further being saturated or unsaturated; alpha-olefins with 8 to 30 carbon atoms; fatty alcohols with 8 to 24 carbon atoms; alkylene oxide adducts of fatty alcohols with 8 to 24 carbon atoms; alkylphenols with 8 to 15 carbon atoms and their alkylene oxide derivatives; fatty acid methyl esters; and combinations of any of the foregoing.

2. The method of claim 1, comprising feeding the $SO_3$/air mixture to only two feed locations.

3. The method of claim 2, further comprising dividing the $SO_3$/air mixture such that the $SO_3$/air mixture introduced at the first feed location is less than a stoichiometric amount for sulfation or sulfonation of the organic liquid raw material, and the remainder of the $SO_3$/air mixture is introduced at the second feed location.

4. The method of claim 3, wherein 50% to 90% of the $SO_3$/air mixture is introduced at the first feed location.

5. The method of claim 3, wherein 70% to 96% of the $SO_3$/air mixture is introduced at the first feed location.

6. The method of claim 3, wherein 80% to 95% of the $SO_3$/air mixture is introduced at the first feed location.

7. The method of claim 3, wherein the second feed location is spaced from the first location downstream in the direction of the falling film of organic liquid raw material in a range of 4% to 30%, based on the length of the reaction tube, or the length of the annular gap reactor.

8. The method of claim 7, wherein the spacing distance is in a range of 5% to 20%, based on the length of the reaction tube or the length of the annular gap reactor.

9. The method of claim 2, comprising introducing said first and second fractions of the $SO_3$/air mixture from a common source of $SO_3$/air mixture in a reactor head, wherein the introduction of the second fraction of the $SO_3$/air mixture is performed with an inserted tube in a tubular reactor or an inserted double tube in an annular gap reactor, whereby the ratio of the cross-sectional area of the inserted tube to that of the tubular reactor, or the ratio of cross-sectional area of the inserted double tube to that of the annular gap, controls the volumetric distribution of the $SO_3$/air mixture from the common source to the first and second feed locations.

10. The method of claim 1, wherein the sulfonation or sulfation of organic liquid raw materials with an $SO_3$/air mixture is carried out in an annular-gap falling-film reactor.

11. The method of claim 1, wherein the sulfonation or sulfation of organic liquid raw materials with an $SO_3$/air mixture is carried out in a multi-tube falling film reactor.

12. The method of claim 1, wherein the first feed location is proximate to the introduction of organic liquid raw material into the falling-film reactor.

13. An apparatus for the sulfonation or sulfation of organic liquid raw materials with an $SO_3$/air mixture, comprising a thin-layer, falling-film reactor comprising
   a tubular reactor comprising at least one reaction tube or an annular-gap reactor in the form of a double cylinder, the tubular reactor or annual gap reactor each having inlet and outlet ends, the inlet end being closer to an inlet opening for introduction of organic liquid raw materials, and the inlet end being a first feed location in gaseous communication with a source of $SO_3$/air mixture;
   and further comprising
      in the case of a tubular reactor, a second, inserted tube comprising inlet and outlet ends, the inlet end being in gaseous communication with a source of $SO_3$/air mixture and the outlet end being inserted into the reaction tube to effect distribution of the $SO_3$/air mixture to at least one secondary feed location within the reaction tube, or
      in the case of an annular-gap reactor, a second, inserted double tube comprising inlet and outlet ends, the inlet end being in gaseous communication with a source of $SO_3$/air mixture and the outlet end being inserted within the annular gap to effect distribution of the $SO_3$/air mixture to a secondary feed location within the annular gap.

14. The apparatus of claim 13, wherein the inserted tube or inserted double tube is configured to introduce the $SO_3$/air mixture at the secondary feed location in a flow direction substantially parallel to the major axis of the inserted tube or inserted double tube.

15. The apparatus of claim 14, wherein the configuration comprises the inserted tube having a solid side wall and an open outlet end, or the inserted double tube having solid side walls and an open outlet end.

16. The apparatus of claim 13, wherein
   the inlet ends of the tubular reactor and the inserted tube are in gaseous communication with a common source of $SO_3$/air mixture in a reactor head and the inlet end of the inserted tube is disposed at a location upstream of the inlet opening for introduction of organic liquid raw materials with respect to the direction of falling flow of the organic liquid raw material in use or
   the inlet ends of the annular gap and the inserted double tube are in gaseous communication with a common source of $SO_3$/air mixture in a reactor head and the inlet end of the inserted double tube is disposed at a location upstream of the inlet opening for introduction of organic liquid raw materials with respect to the direction of falling flow of the organic liquid raw material in use.

17. The apparatus of claim 13, wherein the inserted tube is disposed with respect to the reaction tube, or the inserted double tube is disposed with respect to the annular gap, such that the ratio of the cross-sectional area of the inserted tube to that of the tubular reactor, or the ratio of cross-sectional area of the inserted double tube to that of the annular gap, controls the volumetric distribution of the SO3/air mixture from the common source to the first and second feed locations.

18. The apparatus of claim 17, wherein the inserted tube or double tube is circular, and the diameter ratio of the inserted tube to that of the reaction tube, or the diameter of the inserted double tube to that of the an annular-gap, determines the distribution of the $SO_3$/air mixture to the respective secondary feed location.

19. The apparatus of claim 13, comprising a single inserted tube or a single double tube set for feeding the $SO_3$/air mixture to a secondary feed location.

20. The apparatus of claim 19, wherein the inserted tube or double tube is sized and disposed to divide the $SO_3$/air mixture such that 50% to 90% of the $SO_3$/air mixture is introduced to the first feed location and the remaining fraction is introduced to the second feed location.

21. The apparatus of claim 20, wherein the inserted tube or double tube is sized and disposed to divide the $SO_3$/air mixture such that 70% to 96% of the $SO_3$/air mixture is introduced to the first feed location.

22. The apparatus of claim 21, wherein the inserted tube or double tube is sized and disposed to divide the $SO_3$/air mixture such that 80% to 95% of the $SO_3$/air mixture is introduced to the first feed location.

23. The apparatus of claim 19, wherein the outlet end of the inserted tube or double tube is spaced from the first feed location a distance in a range of 4% to 30%, based on the length of the reaction tube or annular gap.

24. The apparatus of claim 23, wherein the spacing distance is in a range of 5% to 20%, based on the length of the reaction tube or annular gap.

25. The apparatus of claim 13, comprising an annular-gap, falling-film reactor.

26. The apparatus of claim 13, comprising a multi-tube, falling film reactor.

* * * * *